(12) United States Patent
Vento

(10) Patent No.: US 11,439,445 B2
(45) Date of Patent: Sep. 13, 2022

(54) METHODS OF BONE REDUCTION AND FIXATION

(71) Applicant: DYNORIF, LLC, Moreland Hills, OH (US)

(72) Inventor: Joseph Michael Vento, Moreland Hills, OH (US)

(73) Assignee: DYNORIF, LLC, Moreland Hills, OH (US)

( * ) Notice: Subject to any disclaimer, the term of this patent is extended or adjusted under 35 U.S.C. 154(b) by 344 days.

(21) Appl. No.: 16/821,336

(22) Filed: Mar. 17, 2020

(65) Prior Publication Data

US 2020/0297397 A1 Sep. 24, 2020

Related U.S. Application Data

(60) Provisional application No. 62/887,059, filed on Aug. 15, 2019, provisional application No. 62/820,611, filed on Mar. 19, 2019.

(51) Int. Cl.

| | |
|---|---|
| *A61B 17/72* | (2006.01) |
| *A61B 17/80* | (2006.01) |
| *A61B 34/10* | (2016.01) |
| *C22F 1/10* | (2006.01) |
| *C22F 1/00* | (2006.01) |
| *C22C 19/03* | (2006.01) |
| *A61B 17/68* | (2006.01) |

(Continued)

(52) U.S. Cl.
CPC ...... *A61B 17/7225* (2013.01); *A61B 17/8004* (2013.01); *A61B 34/10* (2016.02); *C22C 19/03* (2013.01); *C22F 1/002* (2013.01); *C22F 1/10* (2013.01); *A61B 2017/00526* (2013.01); *A61B 2017/00867* (2013.01); *A61B 2017/564* (2013.01); *A61B 2017/681* (2013.01); *A61B 2034/108* (2016.02)

(58) Field of Classification Search
CPC ..... A61B 17/68; A61B 17/72; A61B 17/7208; A61B 17/7216; A61B 17/7225; A61B 17/80; A61B 17/8004; A61B 2017/564; A61B 2017/681; A61B 2017/00867; A61B 34/10; A61B 2034/108; C22F 1/002; C22F 1/10
See application file for complete search history.

(56) References Cited

U.S. PATENT DOCUMENTS

| | | | |
|---|---|---|---|
| 9,138,274 B1* | 9/2015 | Biesinger | A61B 17/844 |
| 2009/0275946 A1* | 11/2009 | Duncan | A61B 17/1725 |
| | | | 606/62 |

(Continued)

*Primary Examiner* — Eric S Gibson
(74) *Attorney, Agent, or Firm* — Tucker Ellis LLP

(57) ABSTRACT

Provided is a method of open reduction and internal fixation of a bone of a patient using a fixation device. The method includes analyzing the bone to obtain a fracture profile, wherein the fracture profile includes data corresponding to a physical structure of the bone, shaping the fixation device using the data of the fracture profile, heat treating the fixation device by heating the fixation device to a first temperature, cooling the fixation device to a second temperature lower than the first temperature, securing the fixation device to the bone, and heating the fixation device to a third temperature lower than the first temperature and greater than the second temperature to reduce the bone.

20 Claims, 8 Drawing Sheets

(51) Int. Cl.
*A61B 17/00* (2006.01)
*A61B 17/56* (2006.01)

(56) References Cited

U.S. PATENT DOCUMENTS

| | | | | |
|---|---|---|---|---|
| 2010/0063506 | A1* | 3/2010 | Fox | A61F 2/28 606/151 |
| 2012/0324975 | A1* | 12/2012 | Anderson | A61B 17/064 72/324 |
| 2013/0123785 | A1* | 5/2013 | Fonte | A61B 17/7216 606/62 |
| 2015/0230843 | A1* | 8/2015 | Palmer | A61B 17/7291 606/331 |
| 2015/0238238 | A1* | 8/2015 | Cheney | A61B 17/8004 606/281 |
| 2015/0257801 | A1* | 9/2015 | Palmer | A61B 17/8085 606/281 |
| 2015/0374411 | A1* | 12/2015 | Ehmke | A61B 17/7233 606/329 |
| 2016/0310178 | A1* | 10/2016 | Biedermann | A61B 17/7002 |
| 2017/0135706 | A1* | 5/2017 | Frey | A61B 17/1671 |
| 2017/0209193 | A1* | 7/2017 | Hartdegen | A61B 17/8863 |
| 2017/0238981 | A1* | 8/2017 | Madjarov | A61B 17/8085 |
| 2017/0239396 | A1* | 8/2017 | D'Agostino | A61B 17/7275 |
| 2017/0281157 | A1* | 10/2017 | Hartdegen | A61B 17/1775 |
| 2017/0311948 | A1* | 11/2017 | Morgan | A61B 17/0642 |
| 2018/0078293 | A1* | 3/2018 | Hustedt | A61B 17/80 |
| 2018/0092677 | A1* | 4/2018 | Peterson | A61B 17/863 |
| 2018/0263669 | A1* | 9/2018 | Peterson | A61B 17/8888 |
| 2018/0271602 | A1* | 9/2018 | Frey | A61B 34/10 |
| 2018/0311406 | A1* | 11/2018 | Francis | C22F 1/10 |
| 2020/0297397 | A1* | 9/2020 | Vento | C22F 1/10 |
| 2020/0305936 | A1* | 10/2020 | D'Agostino | A61L 27/48 |
| 2021/0267644 | A1* | 9/2021 | Owusu-Danquah | A61B 17/7059 |
| 2021/0308264 | A1* | 10/2021 | D'Agostino | A61K 9/0024 |
| 2022/0015812 | A1* | 1/2022 | Cheney | A61B 17/8004 |
| 2022/0111116 | A1* | 4/2022 | Dewey | B29C 64/209 |

* cited by examiner

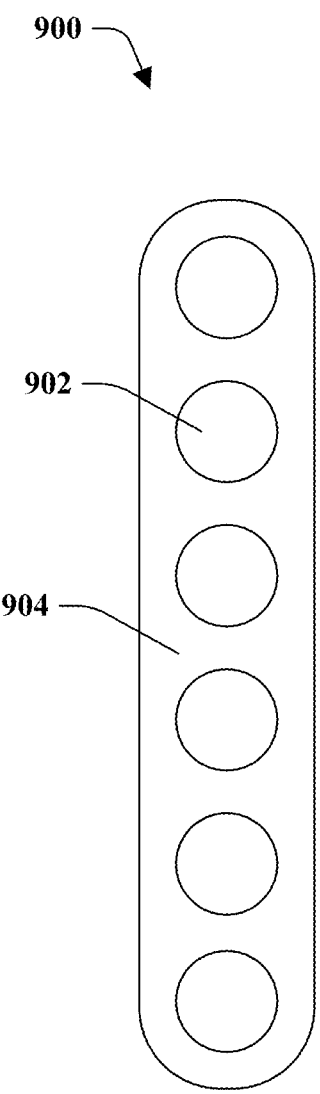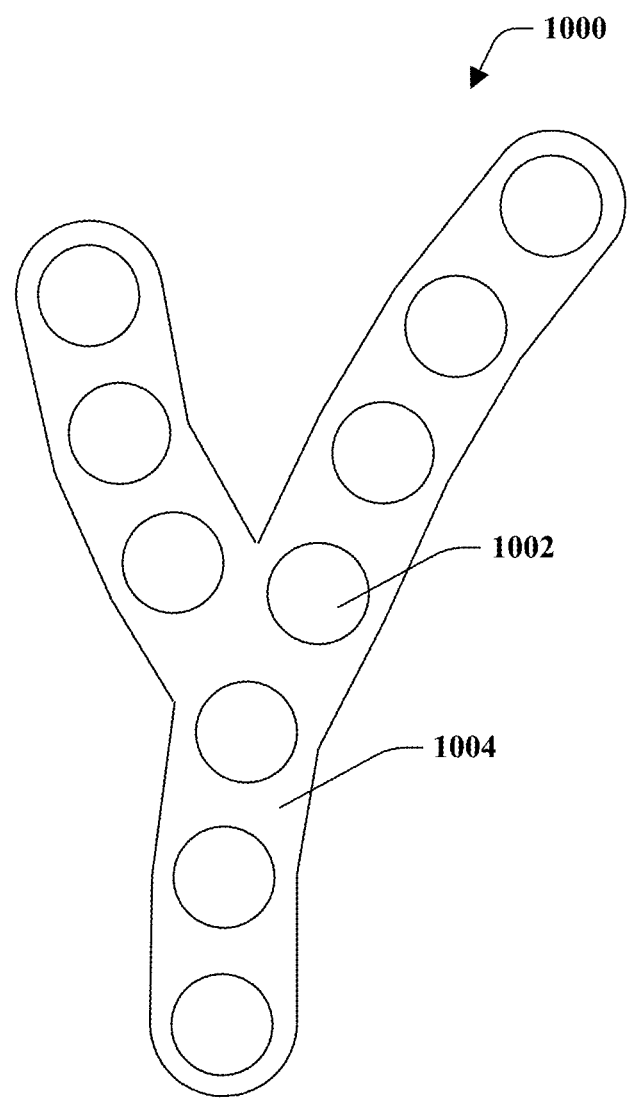
FIG. 9   FIG. 10

METHODS OF BONE REDUCTION AND FIXATION

RELATED APPLICATIONS

This application claims the benefit of U.S. Provisional Application No. 62/887,059 filed Aug. 15, 2019 and U.S. Provisional Application No. 62/820,611 filed Mar. 19, 2019, which are hereby incorporated herein by reference.

FIELD OF INVENTION

The present invention relates generally to methods of reducing bone fractures and deformities using internal fixation devices.

BACKGROUND

Reduction is a term used to describe the process of repairing a fractured or dislocated bone. Reduction can be in the form of open or closed reduction. Open reduction is a process that involves surgically exposing and repairing bones that are fractured, displaced and/or deformed. Closed reduction is a process involves manipulating the fractured bones without surgical access to the fragments. Internal fixation devices are inserted through incisions and may be used to hold the fractured bones in place following reduction of the fracture.

SUMMARY OF INVENTION

The present application relates to a method of open reduction and internal fixation of a bone of a patient using a fixation device. A fractured bone of the patient can be analyzed to obtain a fracture profile that includes data corresponding to a structure of the bone. The fixation device is shaped using the fracture profile and then heat treated to set the fixation device. The fixation can then be cooled and secured to the bone. Once secured to the bone, the fixation device can be heated to reduce the bone.

According to an aspect of the application, a method of open reduction and internal fixation of a bone of a patient using a fixation device is provided. The method comprises analyzing the bone to obtain a fracture profile, wherein the fracture profile includes data corresponding to a physical structure of the bone, shaping the fixation device using the data of the fracture profile, heat treating the fixation device by heating the fixation device to a first temperature, cooling the fixation device to a second temperature lower than the first temperature, securing the fixation device to the bone, and heating the fixation device to a third temperature lower than the first temperature and greater than the second temperature to reduce the bone.

According to another aspect of the application, a method of open reduction and internal fixation of a fractured bone of a patient using a fixation device formed of a shape memory alloy is provided. The method comprises analyzing the fractured bone to obtain a fracture profile, wherein the fracture profile includes data corresponding to a shape and a curvature of the fractured bone, shaping the fixation device using a mold and the data of the fracture profile, heat treating the fixation device by heating the fixation device to place the fixation device in a fixation state, cooling the fixation device to place the fixation device in a positioning state, positioning the fixation device relative to the bone when the fixation device is in the positioning state, and heating the fixation device to return the fixation device to the fixation state to reduce the bone.

According to still another aspect of the application, a method of open reduction and internal fixation of a fractured bone of a patient using an intramedullary fixation device formed of shape memory alloy is provided. The method comprises analyzing the fractured bone to obtain a fracture profile, wherein the fracture profile includes data corresponding to a shape and curvature of the fractured bone, shaping the fixation device using the fracture profile, heat treating the fixation device by heating the fixation device to a first temperature, cooling the fixation device to a second temperature lower than the first temperature, implanting the fixation device into a medullary cavity of the fractured bone, and reducing the fractured bone by heating the fixation device to a third temperature lower than the first temperature and greater than the second temperature to reduce the fractured bone.

The foregoing and other features of the application are described below with reference to the drawings.

BRIEF DESCRIPTION OF THE DRAWINGS

FIG. 9 is an exemplary plate for open reduction and internal fixation.

FIG. 10 is an exemplary plate for open reduction and internal fixation.

DETAILED DESCRIPTION

Figure 1:
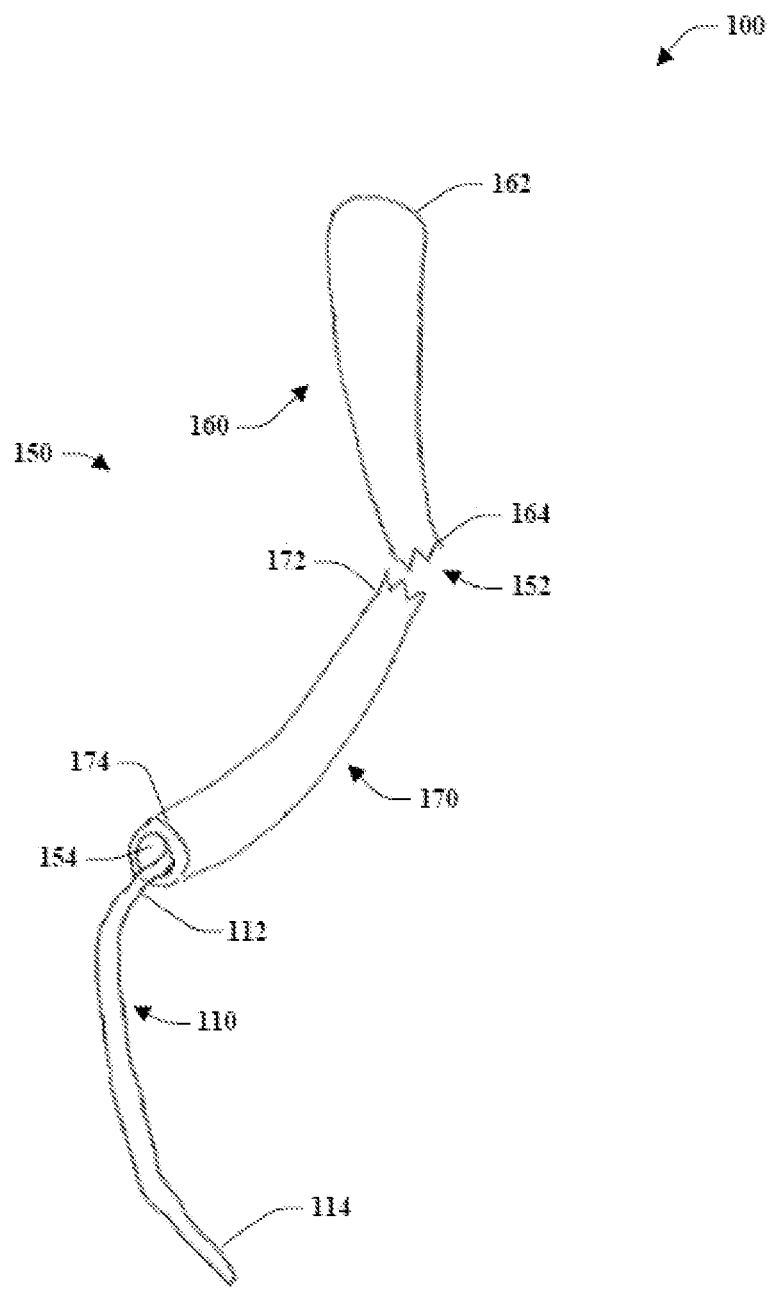
FIG. 1 is an exemplary embodiment of a fractured bone and an internal fixation device.

The principles of the present application relate to a method of open reduction and internal fixation of a bone fracture, dislocation, or deformity. An internal fixation device may be a rod, plate, screw, or other implant, and the method of open reduction and internal fixation will be described below in this context. It will be appreciated that the principles of the application may be applicable to various surgeries for bones or joints of the face, spine, arms, legs, fingers, feet, etc. The present application provides a method of open reduction and internal fixation that may be helpful for complex fractures, comminuted fractures, irregularly shaped bones, deformities, and similar concerns.

Broken bones typically require medical attention to ensure that the bones heal correctly. In some instances bones may break or fracture into multiple fragments and may become misaligned. In the medical profession, reduction is the process of repairing or restoring (i.e., bring back to normal) a bone fracture or dislocation to its original form.

Bone reduction may be either closed or open. Closed reduction is a process that involves manipulating the fractured bones without surgical access to the fragments. Methods of closed reduction may include using a splint, a cast, or any similar device to manipulate the bone into its original form. Open reduction is a process that involves surgically exposing and repairing the fractured bones. Open reduction may be used in situations where the fractured bone would not heal correctly using closed reduction techniques. Open reduction involves surgically exposing the tissues and bone fragments and manipulating the fragments back into place (e.g., by aligning the bone fragments with one another, etc.).

After reduction of the bone fragments, the fragments must be held in place to prevent movement as the bones heal. The process of preventing movement of the bone or bone fragments is referred to as bone fixation. Current methods of fixation include both internal and external fixation techniques. Fixation typically includes attaching rods or plates to bone fragments using screws, for example. In external fixation methods, the rods and/or plates are attached to the bones via screws, but the rods and/or plates remain outside of the body. The rods and/or plates may be attached to an external structure to hold the components and the bone fragments in place.

Internal fixation also includes the use of rods, plates, or similar devices to hold bone fragments in place after a surgery, for example. The rods, plates, or similar devices may be secured to the bone fragments using screws or other methods. In contrast to external fixation, the components of internal fixation are entirely internal to the patient's body. In some instances, rods are installed in the medullary cavity of the fractured bone to hold the bone fragments in place. These are referred to as intramedullary devices and may be shaped or bent according to a bone's specific curvature.

The existing open reduction and internal fixation techniques, while successful in repairing bones to their original state, may also have drawbacks. For example, patients may experience excess bleeding, infection, or soft tissue damage as a result of the surgery. In addition, complex fractures, comminuted fractures, irregular-shaped bones, and deformities may require additional time and effort to align properly and repair. Current open reduction and internal fixation methods may include manually reducing the bone fragments using clamp-like devices to hold the fragments in place before internal fixation. The reduction process can be tedious and difficult when there is a displacement, deformity, segmental bone loss or comminution. In severe fractures, surgeons may spend great amounts of time aligning bone fragments and maneuvering an internal fixation device through or around the bone. The additional time that is required may increase the likelihood of infection, soft tissue damage, or similar complications.

A less invasive method of open reduction and internal fixation would provide many benefits over methods used today. For example, open reduction and internal fixation methods that are less invasive than current methods may require less time to complete, reduce bleeding, reduce chances of infection, cause less soft tissue damage and may improve fracture healing due to, for example, less periosteal stripping for fracture reduction.

The present application describes a method of open reduction and internal fixation. The method may include using a flexible internal fixation device formed from a shape memory alloy. The device may be a rod, plate, screw, or any other necessary shape.

In an example, the device is a flexible intramedullary rod made from a flexible metal alloy or shape memory alloy. The flexible intramedullary rod may be shaped in a desired manner corresponding to a bone segment. The rod may then be inserted into the medullary cavity of a fractured bone to reduce the bone into its original form. When inserting the intramedullary rod into the medullary cavity of the bone, the rod may be in a soft, flexible, and malleable state to allow ease of insertion into the medullary cavity of a fractured bone. The intramedullary rod may return to a hardened, non-flexible state over time, and may change to the desired shape corresponding to the curvature of the bone segment. As the intramedullary rod returns to the desired shape, the bone fragments may be dynamically reduced (i.e., aligned, pulled together, etc.) without manual reduction by a medical professional. The hardened intramedullary rod may hold the bone fragments in place to heal. It should also be appreciated that the flexible intramedullary rod may perform both the reduction and the fixation of a fracture.

In another example, the device is a plate made from a flexible metal alloy or shape memory alloy. The plate may be pre-shaped into a desired manner corresponding to the anatomic configuration of a bone segment. The plate may consist of round and/or slotted screw holes to allow for sliding of the plate during reduction of the bone. The plate may be initially in a soft, flexible, and malleable state to allow ease of securing to the displaced bone. The plate may return to a hardened, non-flexible state over time, and may change to the desired shape corresponding to the original anatomic configuration of the bone segment. As the plate returns to the desired shape, the bone fragments may be dynamically reduced (i.e., aligned, pulled together, etc.) without manual reduction by a medical professional. The hardened plate may hold the bone fragments in place to heal. It should also be appreciated that the plate may perform both the reduction and the fixation of a fracture.

In an example, the flexible metal alloy may be Nickel-Titanium (e.g., Nitinol), having desirable flexibility and shape memory characteristics. Nickel-Titanium is referred to as a shape memory alloy (SMA) having super elastic and shape memory properties. Nickel-Titanium may be composed of near equiatomic Nickel (Ni) and Titanium (Ti) (i.e., about 50:50 Ni and Ti). The shape memory properties of an SMA such as Nickel-Titanium are due to the phase transformations that occur when the SMA is subject to an external stimulus such as a change in temperature. Nickel-Titanium has shape memory properties that exist in two main states (i.e., phases): martensite and austenite. In the martensite state, the Nickel-Titanium may be soft, malleable, and flexible at lower temperatures. In the austenite state, the Nickel-Titanium may be hard, rigid, and non-flexible at higher temperatures. A controlled change in temperature may cause a transformation of the Nickel-Titanium from one state of flexibility to the other.

Nickel-Titanium may also have desirable shape memory characteristics utilized by a process of shape setting (or shape training). Shape setting refers to the process used to form an SMA into a specific shape or geometry. The process involves shaping the Nickel-Titanium material into the desired shape or geometry and heat treating (superheating) the Nickel-Titanium. Superheating the Nickel-Titanium sets or constrains the Nickel-Titanium into the Nickel-Titanium's current shape. After the process of shape setting, the Nickel-Titanium will return to the shape established in the shape setting process by virtue of Nickel-Titanium's shape memory characteristics.

For example, a Nickel-Titanium rod may undergo a shape setting process by shaping the rod to a curvature of a bone and then superheating the bone-shaped Nickel-Titanium rod.

Following the shape setting process, when the rod is sufficiently cooled and transformed into the martensite state, the rod may be soft and flexible. The soft, flexible martensite state may allow the rod to be shaped into a completely new shape. Then, heating the rod to a sufficient temperature may transform the rod into the austenite state, and the rod may return to the original shape from the shape setting process (i.e., corresponding to the curvature of a bone). This process may be repeated as desired.

Turning now to FIG. 1, an open reduction and internal fixation arrangement is shown generally at 100. Arrangement 100 includes a bone 150 and a rod 110 formed of a shape memory alloy as discussed above. The bone 150 may be fractured at location 152, forming a first bone fragment 160 and a second bone fragment 170. The first bone fragment 160 may have a first end 162 and a second end 164. The second bone fragment 170 may have a first end 172 and a second end 174. The rod 110 may be an intramedullary rod for open reduction and internal fixation having a first end 112 and a second end 114. The rod 110 may be inserted into the medullary cavity (e.g., marrow cavity) 154 of the second bone fragment 170.

Figure 2:
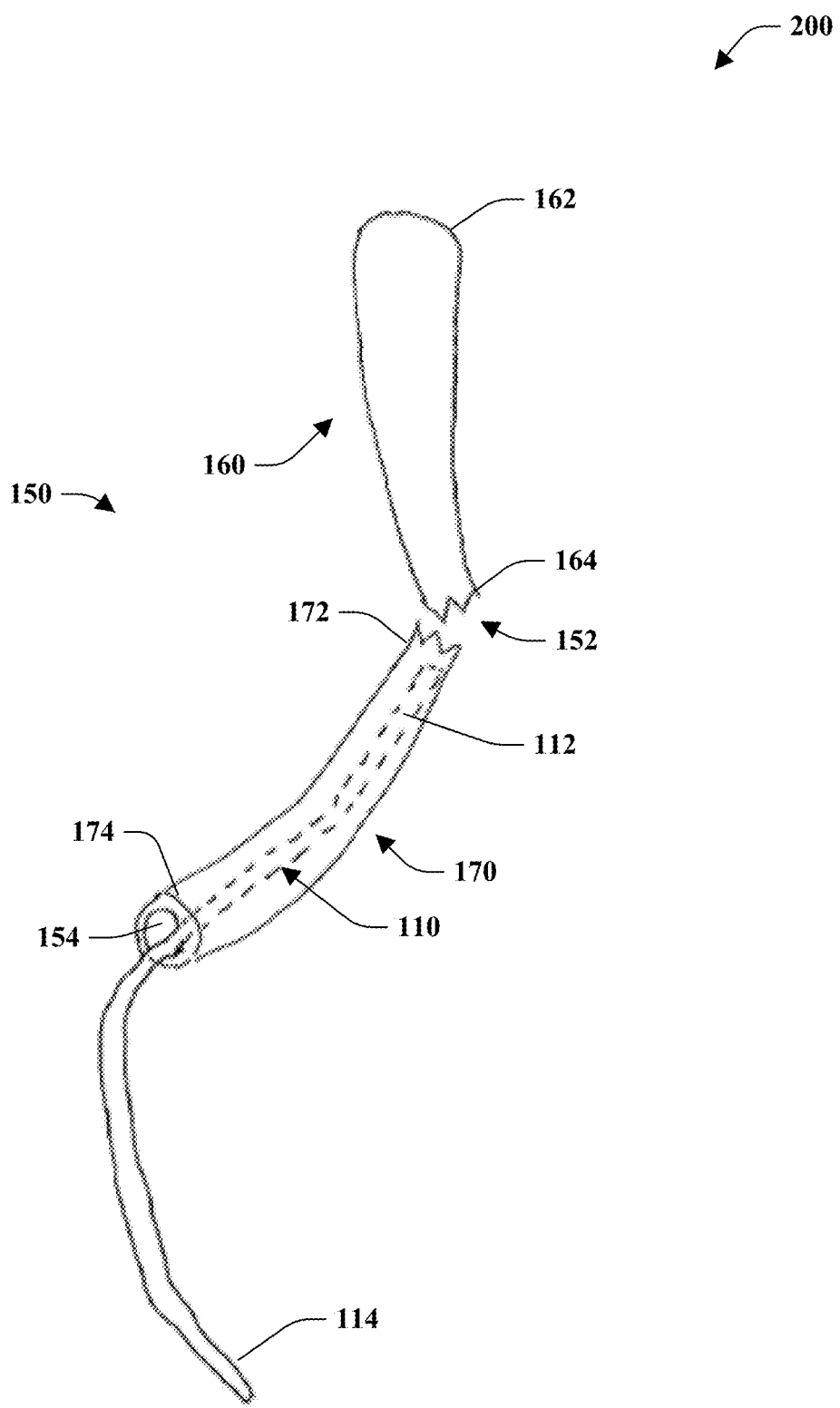
FIG. 2 is an exemplary embodiment of a fractured bone and an internal fixation device partially installed in the fractured bone.
Figure 3:
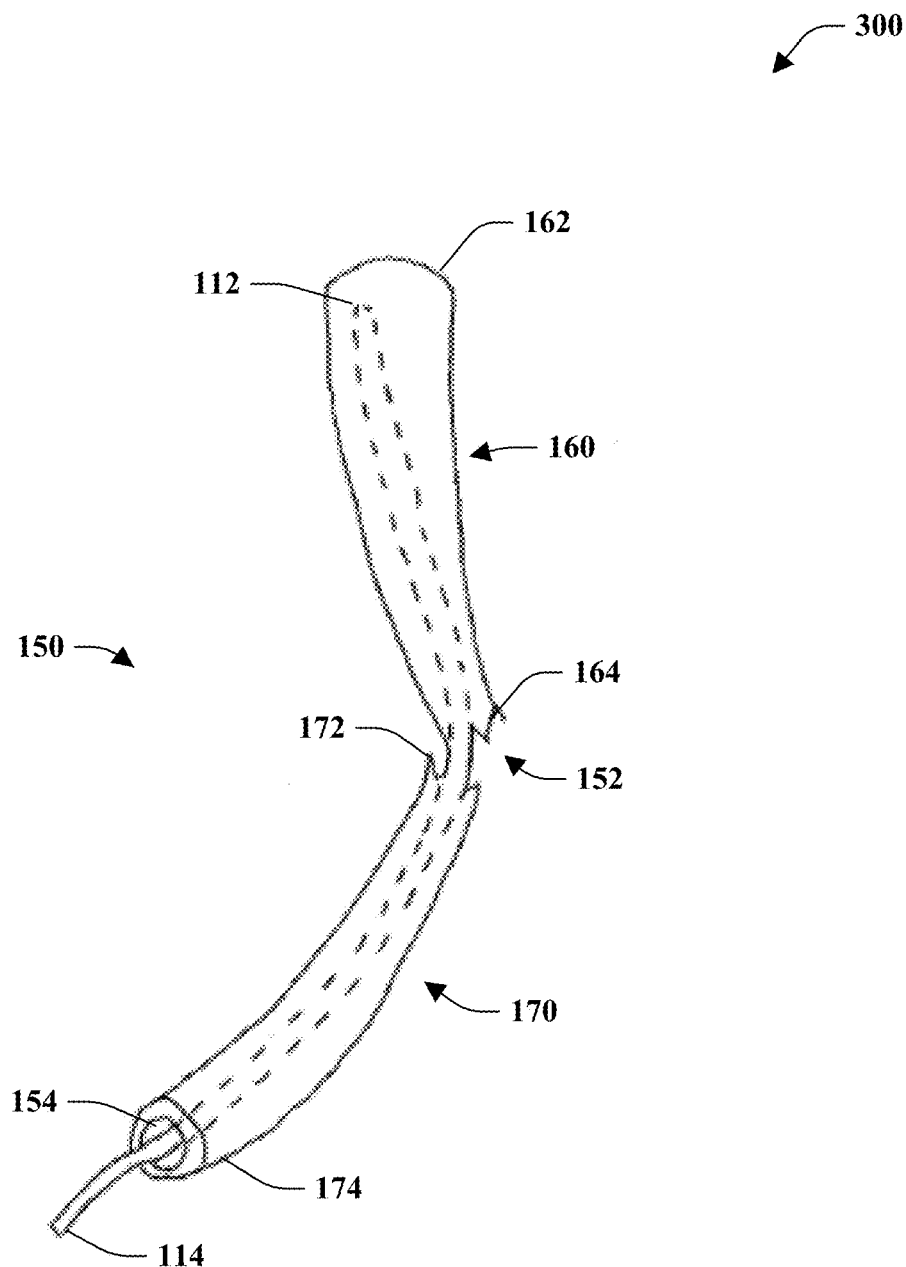
FIG. 3 is an exemplary embodiment of a fractured bone and an internal fixation device installed in the fractured bone.

Turning now to FIG. 2, the rod 110 is shown partially inserted into the medullary cavity 154 of the bone 150. The rod 110 may be shaped into a desired curvature in a shape setting process. Prior to being inserting into the medullary cavity 154 of the bone 150, the rod 110 may be cooled and transitioned to the martensite state. This may allow the rod 110 to be bent and flexed in any desired manner while being inserted into the bone 150. See, for example, the difference in curvature from FIG. 1 to FIG. 2, where the rod 110 may form to the shape of the second bone fragment 170. As shown in FIG. 3, a rod 110 is shown fully inserted into the medullary cavity 154 of the bone 150.

Figure 4:
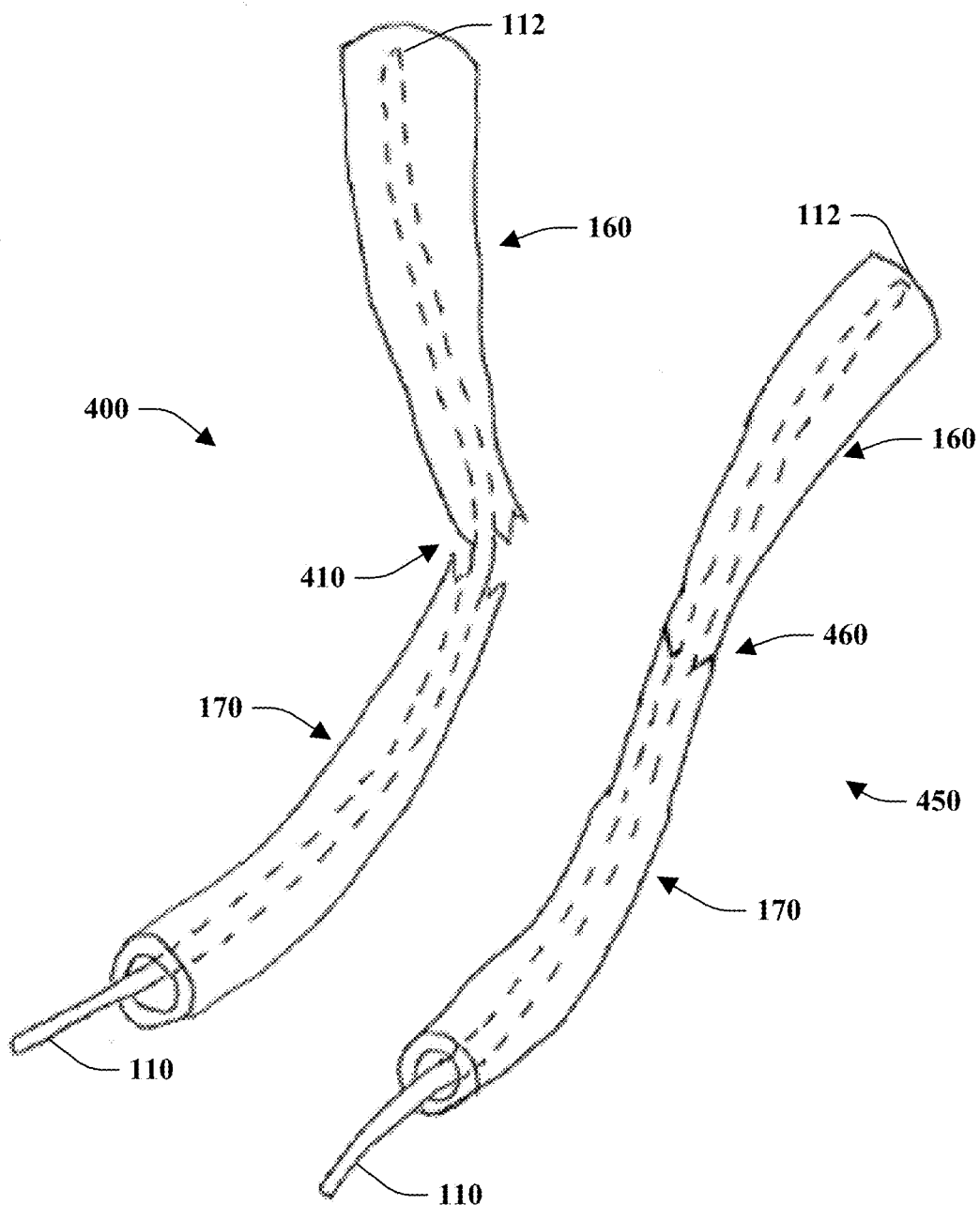
FIG. 4 is an exemplary embodiment of a fractured bone being reduced by an internal fixation device.
Figure 5:
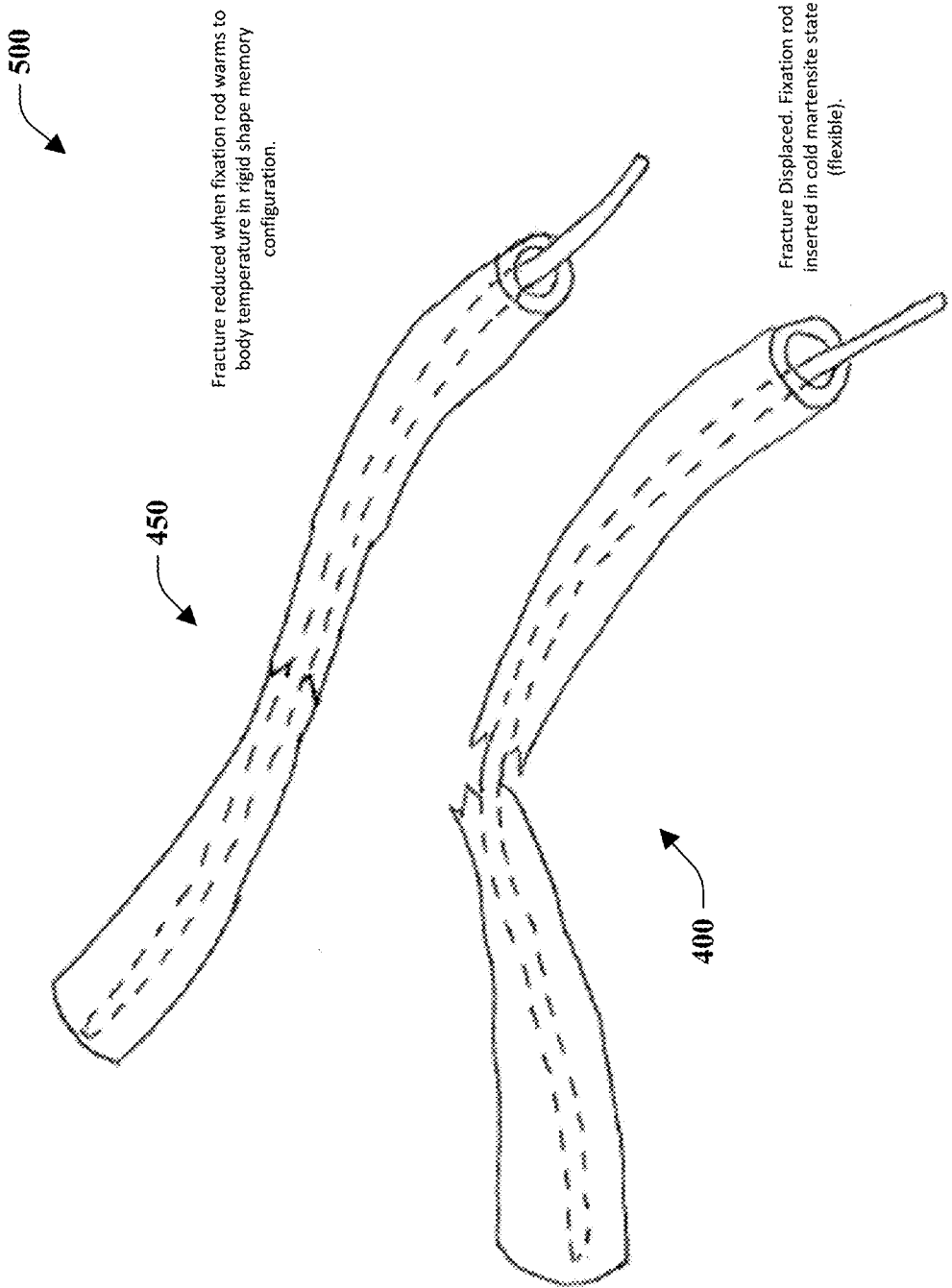
FIG. 5 is an exemplary embodiment of a fractured bone being reduced by an internal fixation device.

Turning now to FIGS. 4 and 5, an open reduction and internal fixation of the bone 150 using the rod 110 is shown. At 400, the rod 110 is shown inserted into the medullary cavity 154 of the bone 150. There is a gap 410 between the first bone fragment 160 and the second bone fragment 170 that may indicate that the reduction of the bone 150 is not yet complete.

The rod 110 (such as an intramedullary Nickel-Titanium rod) may be heated by the body heat of a patient and may transform from the martensite state into the austenite state. As the rod 110 transitions from the martensite state to the austenite state, the rod may begin to harden and form into the curvature set during a previous shape setting process. Shown generally at 450, the rod 110 is shown inserted into the medullary cavity 154 of the bone 150. One will notice that the gap 410 has been closed as indicated at 460, which may indicate the reduction of the bone fracture has been completed.

Figure 6:
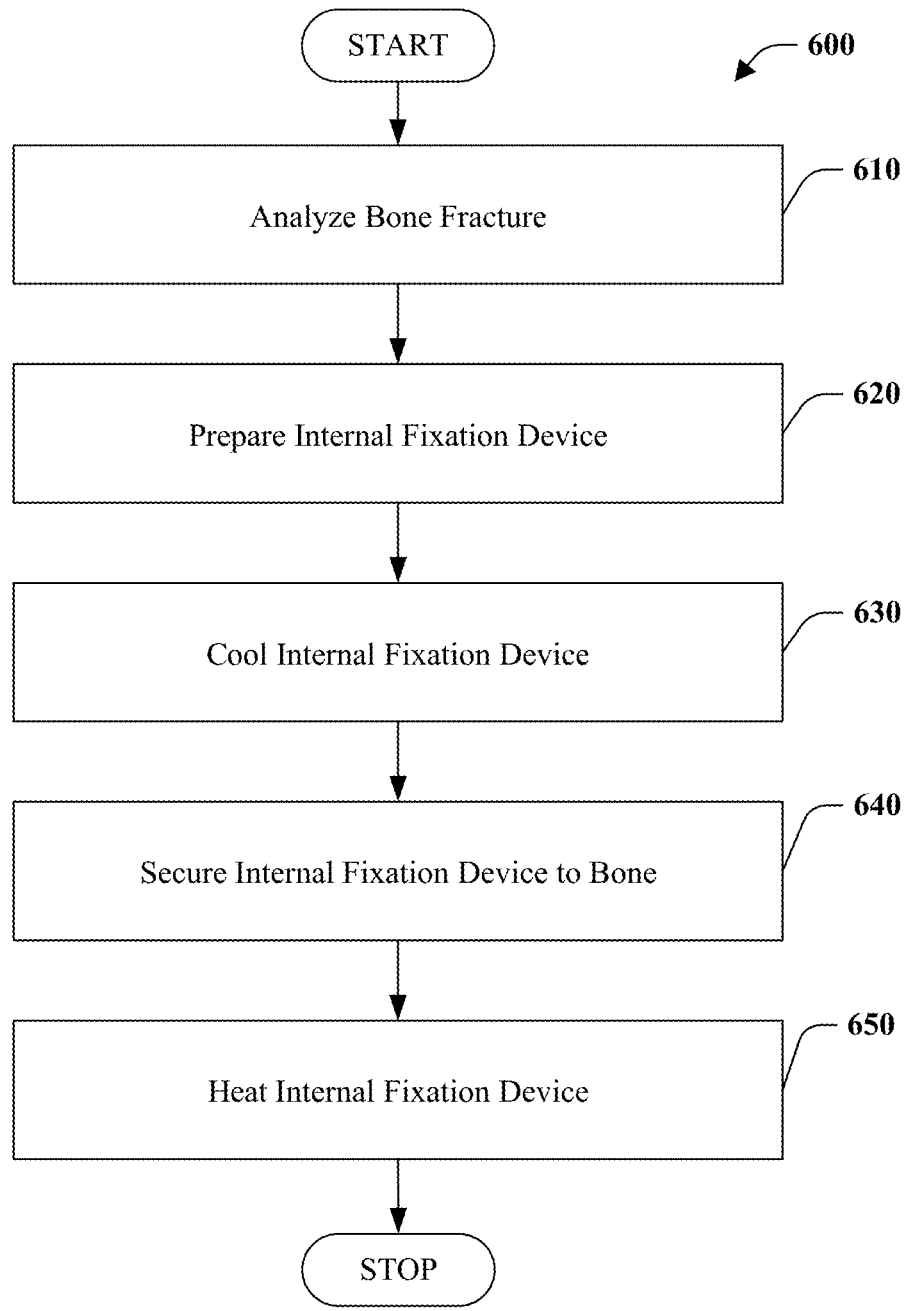
FIG. 6 is an exemplary method of open reduction and internal fixation.

Turning now to FIG. 6, a method for open reduction and internal fixation is shown generally at 600. The method may include the steps of analyzing a bone fracture 610, preparing the internal fixation device 620, cooling the internal fixation device 630, securing the internal fixation device to the bone 640, and warming the internal fixation device 650. By way of example and not limitation, the internal fixation device may be an intramedullary Nickel-Titanium rod, Nickel-Titanium plate, or any other device made of a shape memory alloy or similar material.

In step 610, a bone fracture may be analyzed. The fracture may be analyzed by a medical professional, computer, automated device, or a combination thereof. Information may be gathered relating to the fractured bone such as severity of the fracture, type of fracture, location of the fracture, size of the bone, curvature of the bone, complications surround the bone, and any other relevant information as determined by medical professionals. The information gathered may be used to create a fracture profile corresponding to the fractured bone.

In an example, information regarding a fractured bone may be obtained from a bone contralateral to the fractured bone (e.g., bone on the opposite side). The corresponding left side and right side bones may be similar in their shape and size, and therefore gathering structural information on one bone may give an accurate representation of the structure of other. A three-dimensional image for the fractured bone may be produced using the contralateral non-fractured bone.

By way of example, for a comminuted or open fracture of a left side femur, structural information such as curvature may be difficult to obtain. Structural analysis of the right side femur may be used to estimate the structural information such as curvature of the left side femur. The structural information from the right side femur may be used to create a three-dimension image of the left side femur that may then be used for shape setting an internal fixation device.

In another example, an X-ray, magnetic resonance imaging (MRI), computerized tomography (CT) scan, 3D radiographic reconstructive imaging of the normal contralateral bone or similar procedure may be used to provide structural information and to create a fracture profile. Computer guided surgical imaging may be used to identify fixation points to assure proper placement of the device and accurate reduction in the final state. The fractured bone may also be examined by a medical professional either surgically, or non-surgically to obtain similar information.

In another example, step 610 may include analyzing a non-fractured bone. The bone may be deformed, irregularly shaped, dislocated, or may have any similar complication or combination thereof. The bone may be analyzed by a medical professional, computer, automated device, or a combination thereof. Information may be gathered relating to the bone such as location of the deformity, type of deformity, type of dislocation, size of the bone, curvature of the bone, complications surround the bone, and any other relevant information as determined by medical professionals. The information gathered may be used to create a profile corresponding to the bone in question.

Similarly, information regarding a non-fractured bone may be obtained from a bone contralateral to the non-fractured bone (e.g., bone on the opposite side). The corresponding left side and right side bones may be similar in their shape and size, and therefore gathering structural information on one bone may give an accurate representation of the structure of other. A 3-dimensional image for the non-fractured (i.e., but still damaged, deformed, dislocated, etc.) bone may be produced using the contralateral bone.

In step 620, the internal fixation device may be prepared for open reduction and internal fixation of the fractured bone. In an example, preparation of the device may include selecting an appropriate type of device, size of device, etc. Once a proper internal fixation device is selected, the device may be cut to a specific length, diameter, width, or height according to the fractured bone. The selection of the type, size, or any other characteristics of the device may be based at least in part on the characteristics or fracture profile determined in step 610.

In another example, the internal fixation device may be shaped according to the structural characteristics of the fractured bone. The structural characteristics may be determined from step 610, for example, and may include curvature of the fractured bone. The internal fixation device may be shaped according to the curvature of the fractured bone, or may be shaped according to the curvature of a non-fractured bone contralateral to the fractured bone. For internal fixation devices, such as rods, it may be desirable to match the curvature of the fractured bone.

The internal fixation device may be an intramedullary Nickel-Titanium rod, for example. The Nickel-Titanium rod may be shaped according to step 620 to allow insertion into the medullary cavity of a fractured bone for open reduction and internal fixation. The process of shape setting may be used to finalize the shape and curvature of the Nickel-Titanium rod and establish the shape into memory. Shape setting may involve shaping the rod into a desired geometric structure or shape and heat treating the Nickel-Titanium rod. To hold the rod (or any other internal fixation device) in a desired shape during the shape setting process, a mandrel, clamp, mold, vice, or similar device may be used.

The Nickel-Titanium (or any other SMA) device, may be heat treated (e.g., superheated) using any suitable heat treatment method. Suitable heat treatment methods may include using a molten salt bath, a fluidized bed, an air furnace, a heated die, an air convection furnace, or any similar method. The Nickel-Titanium device may be heat treated while the shape is held in place using a mandrel, clamp, mold, vice, or similar heat resistant item. The time and temperature at which the Nickel-Titanium device is heat treated may vary on the size, shape, thickness, or type of device. In one example, the heat treatment process may heat at a temperature of 400° C. for two minutes. In another example, the heat treatment process may heat at a temperature of 500° C. for five minutes. It will be appreciated that the temperature, heat time, and heat treatment method may be varied using sound engineering judgment. Varying the various factors (e.g., temperature, time, heat treatment method, etc.) in the heat treatment process may affect the properties of the Nickel-Titanium rod such as, but not limited to, flexibility, rigidity, and state transition times (i.e., how fast the rod transitions from the martensite to austenite states; also vice versa).

Following the heat treatment process, the Nickel-Titanium device may be rapidly cooled. Rapid cooling may be desirable following the heat treatment process of step 620 to finalize the shape setting. Methods of rapid cooling may include, but are not limited to, air cooling, water cooling, ice cooling, or a combination thereof.

Shown in step 630, the internal fixation device may be cooled to place the device in a flexible state. For an internal fixation device made from a shape memory alloy such as Nickel-Titanium, cooling the device may cause the device to transition from an austensite state to a martensite state. The cooling may take place prior to implanting the internal fixation device into a medullary cavity of a bone. Cooling the internal fixation device may place the device into a soft and flexible state allowing the device to be easily maneuverable during surgery, for example.

In an example, the internal fixation device is a Nickel-Titanium intramedullary rod that has been prepared in a manner consistent with step 610 and step 620. The intramedullary rod may be sized and shaped according to the characteristics of a fractured bone. The intramedullary rod may be cooled such that the rod transitions from an austensite state to a martensite state to prepare for an open reduction and internal fixation surgery. The intramedullary rod may be hollow in the center (e.g., may be a tube). To cool the intramedullary rod, one may send a compressed gas such as nitrogen through the center of the intramedullary rod.

In another example, the intramedullary rod may be cooled by placing the rod into a refrigeration system. In yet another example, the intramedullary rod may be cooled using ice, dry ice, ice packs, or similar devices. It should be appreciated that the intramedullary rod may be cooled in any manner according to sound medical or engineering judgment.

The intramedullary rod, or any internal fixation device, may be cooled for any duration of time or to any desired temperature. The rigidity or flexibility may be varied by varying the temperature of the device. For example, an intramedullary rod may be cooled with liquid Nitrogen for sixty seconds to obtain a desired rigidity or flexibility. The rod may be cooled further if the rod is more rigid than desired. Cooling the device to a lower temperature may make the device more flexible and less rigid. It should be appreciated that the device may be cooled as much or as little as required to obtain the desired flexibility or rigidity or the device.

In an example, the fixation device may be cooled to a temperature that is less than the temperature used in the heat treatment process and also less than the temperature of the human body (e.g., less than 98.6° F.).

Shown in step 640, the internal fixation device may be secured to the fractured bone. The internal fixation device may be any device such as a rod, a plate, a screw, a bolt, or any similar device according to sound medical judgment. The internal fixation device may also be secured to the fractured bone in any manner consistent with proper medical practice.

In an example, the internal fixation device is a Nickel-Titanium intramedullary rod. The rod may be prepared and cooled according to steps 610, 620, and 630. The intramedullary rod may be secured to the fractured bone by implanting the rod into the medullary cavity of the fractured bone. The rod may be secured and free from movement by friction or an additional device such as a screw or bolt. The rod may be designed such that the diameter of the rod corresponds to the opening of the medullary cavity of the bone so that the rod is held in place by friction between the rod and the bone.

Open reduction and internal fixation may be performed to implant the intramedullary rod into the medullary cavity of a fractured bone. The rod may be sufficiently cooled to place the rod into the flexible martensite state. Installing the rod into the medullary cavity of the fractured bone may be completed with less effort when the rod is soft and flexible. This may allow a surgeon to better maneuver the rod through the medullary cavity of a bone, for example.

One will appreciate the advantages over current intramedullary devices that are less flexible and forgiving. In some fractures (especially severe fractures), fixation of an intramedullary rod may be difficult and time consuming. Surgeons may have to align the intramedullary rod with the corresponding fragments of the fractured bone and slowly feed the rod through the bone. The process may require that the bone fragments are aligned accurately to ensure that the rod passes through the medullary cavity without catching on edges of the fractured bone. A Nickel-Titanium intramedullary rod, unlike intramedullary rods used in current practice, may not require a surgeon to line up bone fragments with great accuracy. It may require only that the bone fragments are close enough to allow the intramedullary rod to pass through. The Nickel-Titanium intramedullary rod may flex between bone fragments making the fixation procedure less tedious and more forgiving.

Shown in step 650, the internal fixation device may be heated. Heating the internal fixation device may transition the device from a soft, flexible, martensite state to a hard, rigid, austenite state. As the internal fixation device transitions from a martensite state to an austenite state (i.e., as the device hardens), a fracture may be reduced without manual reduction by a surgeon or medical professional. The temperature to which the fixation device is heated to may be less than the temperature used in the heat treatment process of step 620, but greater than the temperature of the cooling process 630. In an example, the fixation device is heated to the temperature of a human body (e.g., 98.6° F.).

In an example, the internal fixation device is a Nickel-Titanium intramedullary rod. The rod may be prepared, cooled, and secured to a bone according to steps 610, 620, 630, and 640. The intramedullary rod may be heated naturally by a patient's body heat as the rod is secured into the medullary cavity of a fractured bone. As the rod heats (e.g., to a patient's body temperature) and hardens, the rod may reduce the fractured bone without manual reduction from a medical professional. In a fracture having at least two bone fragments, the bone fragments may be a distance apart at the onset of the procedure and may be reduced to their original position and orientation as the intramedullary rod hardens.

In some instances, the internal fixation device, such as a Nickel-Titanium intramedullary rod, may harden more quickly than desired. For example, the device may harden before a surgeon has fully implanted the device into the medullary cavity of a fractured bone. To soften the device (i.e., transition to the martensite state), liquid nitrogen may be used to re-cool the device. In a device, such as a hollow rod, the nitrogen may be sent through the rod to sufficiently cool and soften the rod. Sound medical judgment may be used to determine to amount of nitrogen required in the procedure as to not harm the patient. It should be appreciated that the device may be cooled in any other suitable manner such as using other compressed gases, non-compressed air, or by others.

Figure 7:
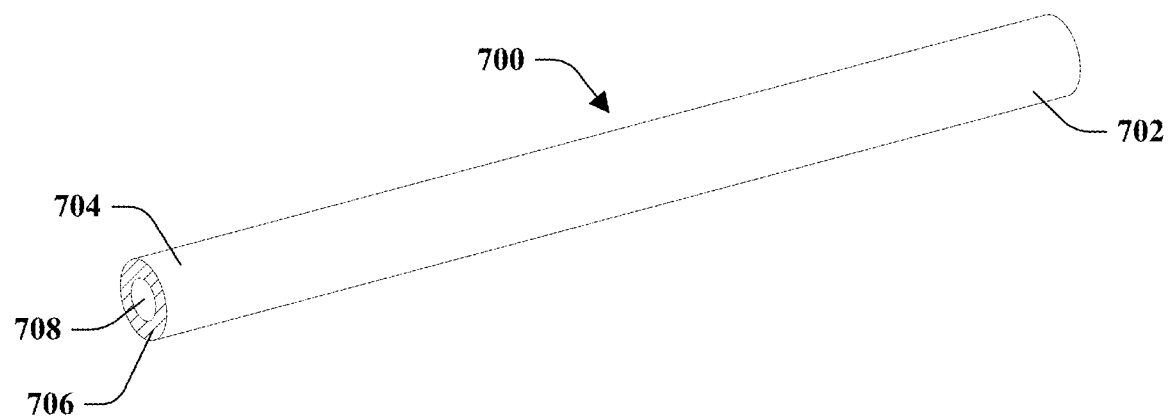
FIG. 7 is an exemplary intramedullary rod for open reduction and internal fixation.

Turning to FIG. 7, an exemplary intramedullary rod 700 is shown. The rod 700 may have a first end 702 and a second end 704 and may be any suitable length or diameter. The rod 700 may also be hollow having a throughpassage 708 of any suitable diameter extending from the first end to the second end. The thickness of the outer wall 706 may be any suitable thickness. The intramedullary rod 700 may be formed of any suitable material such as a shape memory alloy (e.g., Nickel-Titanium).

Figure 8:
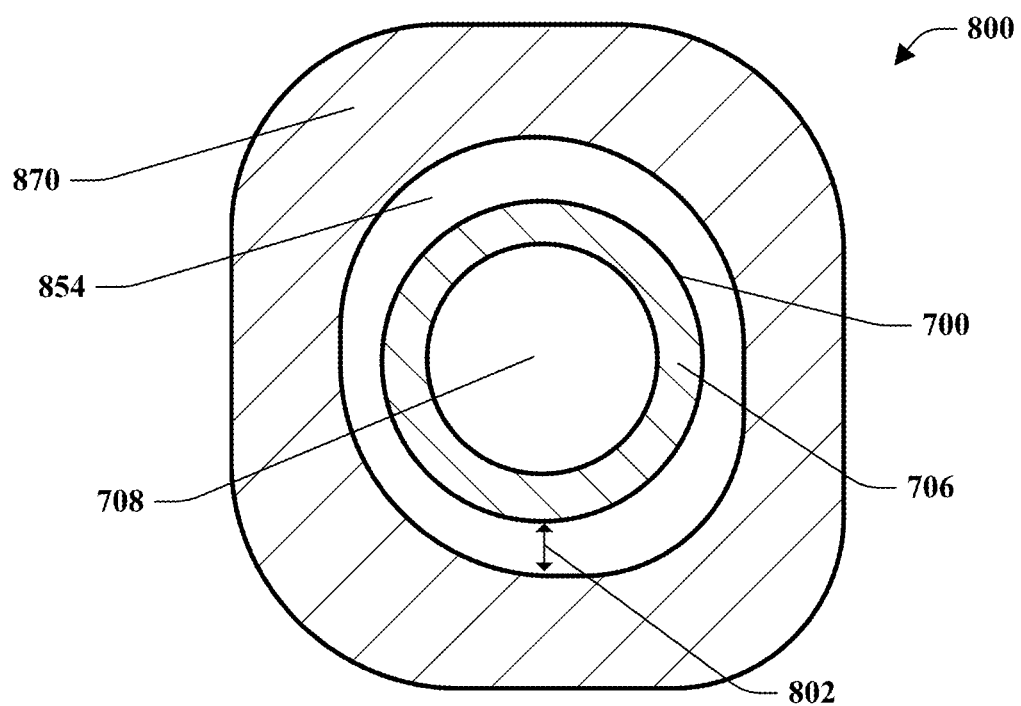
FIG. 8 is a cross-sectional view of an intramedullary rod implanted in a medullary cavity of a bone.

Turning to FIG. 8, an exemplary intramedullary rod 700 is shown implanted into a bone 870. The bone 870 may by hollow and include a medullary cavity 854 to which the intramedullary rod 700 may be implanted. The intramedullary rod 700 may be inserted into the medullary cavity 854 of the bone 870 leaving a gap 802 of any suitable distance. The gap 802 may be sufficiently small to allow the intramedullary rod 700 to remain inside the medullary cavity 854 by friction (e.g., pressure fit, interference fit, etc.) The gap 802 may also be sufficiently large to allow the intramedullary rod 700 to be maneuvered through the medullary cavity 845 during an open reduction and internal fixation procedure.

In an example, the intramedullary rod 700 is formed of a shape memory alloy. After the intramedullary rod 700 is at least partially implanted into the medullary cavity 854, the intramedullary rod 700 may heat to a body temperature of a patient, and may become at least partially rigid. To transform the intramedullary rod 700 into a soft martensite state, the intramedullary rod 700 may be cooled using any suitable method. A suitable method may involve sending a compressed gas such as nitrogen through the opening 708 of the intramedullary rod 700. The gas may flow through the throughpassage 708 and cool the intramedullary rod 700 to a sufficient temperature (e.g., at least below a patient's body temperature of 98.6° F.). As the intramedullary rod 700 is cooled, the rod may return to a soft and flexible martensite state.

In an example, the temperature of the liquid nitrogen may be below freezing (e.g., below thirty-two ° F.) and may be harmful to a patient. Sound medical or engineering judgment may be applied to determine the appropriate amount of cooling that is required. A maximum amount of cooling or liquid nitrogen may also be determined such that a patient is not harmed in the process. To accomplish these determinations, the amount of liquid nitrogen that is released may be metered so that a maximum amount is not reached and the patient is not harmed.

Turning to FIG. 9, and exemplary plate 900 for internal fixation is shown. The plate may have a body 904 having through holes 902. The body 904 may be any suitable thickness and may be comprised of any suitable material such as Nickel-Titanium. Pins, nails or screws may be inserted into the holes 902 to secure the plate 900 to the exterior surface of a bone. The plate 900 may be formed of any suitable material such as a shape memory alloy (e.g., Nickel-Titanium). Turning to FIG. 10, and exemplary plate 1000 for internal fixation is shown. The plate may have a body 1004 having through holes 1002. The body 1004 may be any suitable thickness and may be comprised of any suitable material. Nails or screws may be inserted into the holes 1002 to secure the plate 1000 to the exterior surface of a bone. The plate 1000 may be formed of any suitable material such as a shape memory alloy (e.g., Nickel-Titanium). FIG. 10 shows an example of a plate configuration that could be used for flat bones.

It should be appreciated that the internal fixation devices described herein may be used for open reduction and internal fixation for any suitable bone having any number of fragments for any number of medical issues. For example, an internal fixation device according to the present application may be used in a medical procedure for a fractured bone having any type of fracture (e.g., greenstick, transverse, spiral, oblique, compression, comminuted, segmental, etc.). The fracture may comprise any number of fragments and may be a fracture of any type of bone. The internal fixation device may also be used in procedures relating to irregularly shaped bones, deformities, and dislocations.

The present application may be applied to either internal or external fixation devices. The devices may be any shape, size, thickness, or material. For example, the devices may be a rod, a plate, a screw, a nail, or any similar device. The devices may be hollow, solid, or a combination thereof. The devices may be made of any suitable material, including shape memory alloys such as Nickel-Titanium. Other suitable shape memory alloys may include copper-aluminum-nickel, or alloys created from others alloys such as zinc, copper, gold, and iron.

Although certain embodiments have been shown and described, it is understood that equivalents and modifications falling within the scope of the appended claims will occur to others who are skilled in the art upon the reading and understanding of this specification.

What is claimed is:

1. A method of open reduction and internal fixation of a bone of a patient using a fixation device, the method comprising:
   analyzing the bone to obtain a fracture profile, wherein the fracture profile includes data corresponding to a physical structure of the bone;

shaping the fixation device using the data of the fracture profile;

heat treating the fixation device by heating the fixation device to a first temperature;

cooling the fixation device to a second temperature lower than the first temperature;

securing the fixation device to the bone; and heating the fixation device to a third temperature lower than the first temperature and greater than the second temperature to reduce the bone.

2. The method according to claim 1, wherein heating the fixation device to the third temperature is caused at least partly by body heat of the patient.

3. The method according to claim 1, wherein the fixation device is a shape memory alloy.

4. The method according claim 3, wherein the fixation device is in a flexible state at the second temperature and rigid state at the third temperature.

5. The method according to claim 1, wherein the fixation device is made from Nickel-Titanium.

6. The method of claim 1, wherein the fixation device is a rod for internal fixation.

7. The method of claim 1, wherein the fixation device is a plate for internal fixation.

8. The method according to claim 1, wherein the fixation device is an intramedullary Nickel-Titanium rod and securing the fixation device to the bone includes implanting the fixation device into a medullary cavity of the bone.

9. The method according to claim 1, wherein analyzing the bone to obtain a fracture profile further includes analyzing a second bone contralateral to the bone, the fracture profile corresponding to at least a portion of physical structure of the second bone.

10. The method of claim 1, wherein shaping the fixation device includes placing the fixation device in a mold, the fixation device remaining in the mold for shape setting and heat treating.

11. The method of claim 1, further including re-cooling the fixation device using a compressed gas after the fixation device is at least partially secured to the bone, wherein re-cooling the fixation device using a compressed gas transitions the fixation device to a flexible state.

12. The method of claim 1, wherein the first temperature is at least 450 degree Celsius.

13. A method of open reduction and internal fixation of a fractured bone of a patient using a fixation device formed of a shape memory alloy, the method comprising:

analyzing the fractured bone to obtain a fracture profile, wherein the fracture profile includes data corresponding to a shape and a curvature of the fractured bone;

shaping the fixation device using a mold and the data of the fracture profile;

heat treating the fixation device by heating the fixation device to place the fixation device in a fixation state;

cooling the fixation device to place the fixation device in a positioning state;

positioning the fixation device relative to the bone when the fixation device is in the positioning state; and heating the fixation device to return the fixation device to the fixation state to reduce the bone.

14. The method according to claim 13, wherein heating the fixation device to return the fixation device to the fixation state is caused at least partly by body heat of the patient.

15. The method according to claim 13, further including re-cooling the fixation device using a compressed gas to transition the fixation device to or toward the positioning state when the fixation device has been at least partially positioned relative to the bone.

16. The method according to claim 15, wherein the compressed gas is liquid nitrogen.

17. The method of claim 13, wherein the fixation device is a rod for internal fixation.

18. A method of open reduction and internal fixation of a fractured bone of a patient using an intramedullary fixation device formed of shape memory alloy, the method comprising:

analyzing the fractured bone to obtain a fracture profile, wherein the fracture profile includes data corresponding to a shape and curvature of the fractured bone;

shaping the fixation device using the fracture profile;

heat treating the fixation device by heating the fixation device to a first temperature;

cooling the fixation device to a second temperature lower than the first temperature;

implanting the fixation device into a medullary cavity of the fractured bone; and reducing the fractured bone by heating the fixation device to a third temperature lower than the first temperature and greater than the second temperature to reduce the fractured bone.

19. The method according to claim 18, wherein heating the fixation device to the third temperature is caused at least partly by body heat of the patient.

20. The method according to claim 18, wherein the fixation device is a shape memory alloy, and wherein the fixation device is in a flexible state at the second temperature and rigid state at the third temperature.

* * * * *